United States Patent [19]

Schleich et al.

[11] 4,254,281

[45] Mar. 3, 1981

[54] NOVEL VITAMIN A ACETATE PROCESS

[75] Inventors: Kuno Schleich, Zollikerberg; Hansjörg Stoller, Reinach, both of Switzerland

[73] Assignee: Hoffmann-La Roche Inc., Nutley, N.J.

[21] Appl. No.: 60,698

[22] Filed: Jul. 25, 1979

Related U.S. Application Data

[63] Continuation of Ser. No. 814,816, Jul. 12, 1977, abandoned.

[30] Foreign Application Priority Data

Jul. 26, 1976 [CH] Switzerland ..................... 9524/76

[51] Int. Cl.$^3$ .................... C07C 67/00; C07C 175/00
[52] U.S. Cl. .................................................. 560/260
[58] Field of Search ........................................ 560/260

[56] References Cited

U.S. PATENT DOCUMENTS

| | | | |
|---|---|---|---|
| 2,957,933 | 10/1960 | Pommer et al. | 560/260 |
| 3,671,575 | 6/1972 | Weinstock | 560/260 |
| 3,732,287 | 5/1973 | Himmele et al. | 560/260 |
| 3,932,485 | 1/1976 | Surmatis | 560/260 |
| 4,081,470 | 3/1978 | Schleich et al. | 560/260 |

FOREIGN PATENT DOCUMENTS

1279677 6/1969 Fed. Rep. of Germany .
1168639 10/1969 United Kingdom .

OTHER PUBLICATIONS

Houben–Weyl, vol. V/1d, p. 93.

*Primary Examiner*—Paul J. Killos
*Attorney, Agent, or Firm*—Jon S. Saxe; Bernard S. Leon; George W. Johnston

[57] ABSTRACT

There is disclosed a novel process for the preparation of vitamin A acetate whereby γ-acetoxy-tiglic aldehyde is reacted with the salt formed by the reaction of vinyl-β-ionol, triphenylphosphine and an acid.

6 Claims, No Drawings

NOVEL VITAMIN A ACETATE PROCESS

This is a continuation of application Ser. No. 814,816, filed July 12, 1977, now abandoned.

DESCRIPTION OF THE INVENTION

The present invention relates to a process for the manufacture of vitamin A acetate. The process in accordance with the invention comprises reacting the salt formed by the reaction of vinyl-β-ionol and triphenylphosphine with an aqueous solution of an acid selected from sulfuric acid, a bisulfate, phosphoric acid or hydrochloric acid, with γ-acetoxytiglic aldehyde.

The vitamin A acetate process provided by the present invention is particularly advantageous over prior art processes in that the instant process may be carried out in water, the cheapest of solvents. Furthermore, by virtue of the fact that the vitamin A acetate, when formed, precipitates from the reaction solution, unwanted side reactions (and by-products) are avoided. The use of water as a solvent allows for a very heat efficient system by enabling the process to be conducted at room temperature.

Another advantage realized by the instant process is the obtention of only two vitamin A acetate isomers viz., the all trans and the 11-cis isomers, with the all trans isomers predominating—67–75%. The all trans product is readily separable from the crude reaction product without the need for isomerization.

The salts used as the starting material in the present process are formed by the reaction of vinyl-β-ionol and triphenylphosphine with an acid selected from sulfuric acid, a bisulfate, phosphoric acid or hydrochloric acid. The salt formed may be referred to as the corresponding β-ionylidenethyltriphenylphosphonium salts such as, for example, β-ionylidenethyltriphenylphosphonium chloride, β-ionylidenethyltriphenylphosphonium bisulfate and the like. Illustrative of the bisulfates that may be used are alkali metal bisulfates, such as sodium and potassium bisulfate, and ammonium bisulfate.

The presence of a base during the reaction of such a β-ionylidenethyltriphenylphosphonium salt with γ-acetoxytiglic aldehyde is required. Particularly preferred bases are the hydroxides of alkali or alkaline earth metals. The hydroxides of sodium, potassium, lithium, barium, calcium, and magnesium are generally used. Other bases that may be employed are alkali metal and alkaline earth metal carbonates (employing the aforementioned such metals), ammonia and organic amines, particularly trialkylamines such as triethylamine. Lower alkyl primary and tertiary amines may also be employed. (The term "lower alkyl" means a straight or branched chain hydrocarbon having from 1–8 carbon atoms.) It has been found to be especially convenient to carry out the reaction in the presence of a base having a pK-value of less than about 13, preferably less than about 11, generally in the range of pK 8–10. The base of preference is either ammonia or an alkali metal carbonate, particularly potassium carbonate.

Preferably, the reaction is carried out in the absence of light, under an inert atmosphere such as argon and nitrogen. Additionally, the addition of an antioxidant to the reaction mixture has been found to be helpful to the process (although not an essential). Preferred antioxidants are butylated hydroxytoluene (BHT) or butylated hydroxyanisole (BHA).

The present process can be carried out either batchwise or continuously.

The reaction can be carried out in a temperature range from above the freezing point of the reaction mixture up to about 100° C. A preferred temperature range for the reaction ranges from about 0° C. to 50° C. When a salt formed by the reaction of vinyl-β-ionol and triphenylphosphine with sulfuric acid, a bisulfate or phosphoric acid is used as the starting material, then the reaction thereof with γ-acetoxytiglic aldehyde is generally carried out at about room temperature. On the other hand, when a salt formed by the reaction of vinyl-β-ionol and triphenylphosphine with hydrochloric acid is used as the starting material, then it is convenient to carry out the reaction with the γ-acetoxytiglic aldehyde at about 35° C. to about 45° C.

The reaction time depends on the temperature at which the reaction is carried out. At low temperatures (about and below 0° C.) a reaction time of between 4 and 20 hours is usual in the case of the sulfates and a reaction time of 1 to 2 hours is usual in the case of the chlorides.

Although the concentration of the salt in the aqueous solution can vary within wide limits, a concentration of about one part of salt to two parts of water has been found to be particularly preferred.

The following examples illustrate the present invention. All temperatures are in degrees Centigrade.

EXAMPLE 1

16.9 g. of β-ionylidenethyltriphenylphosphonium hydrogen sulfate are added at 0° C. to 40 ml. of water. The milky solution which is obtained is neutralized with a solution of 7.46 g. of potassium carbonate in 20 ml. of water. After the addition of about 6 ml. of the potassium carbonate solution, a pH of 5 is attained. The clear solution is then treated with 4.5 g. of γ-acetoxytiglic aldehyde and the remaining potassium carbonate solution is added dropwise within 20 minutes. In so doing, vitamin A acetate, as well as triphenylphosphine oxide, separate out.

The solution is stirred at 0° C. for 14 hours. At the end of the reaction the pH amounts to approximately 11.0. The solution is brought to pH 8 with ca 10 ml. of 2 N sulfuric acid, subsequently transferred into a separating funnel with 100 ml. of methanol and extracted three times with 100 ml. of n-hexane each time. The combined hexane phases are washed with 50 ml. of methanol and water (80:20).

After drying and evaporation in a water jet vacuum (about 1 hour), there remain 10.0 g. of vitamin A acetate of which 76.8% consists of all-trans vitamin A acetate and 22.8% consists of 11-cis vitamin A acetate. The remaining 0.4% consists of equal amounts of 11,13-di-cis vitamin A acetate and 9-cis vitamin A acetate. The chemical yield thus amounts to 100%.

EXAMPLE 2

16.9 g. of β-ionylidenethyltriphenylphosphonium hydrogen sulfate and 4.5 g. of γ-acetoxytiglic aldehyde are added at room temperature to 30 ml. of water. To the resulting solution are added dropwise 7.45 g. of potassium carbonate in 10 ml. of water. After the addition of 3 ml. of the potassium carbonate solution (within 10 minutes), the solution is neutral. The remaining potassium carbonate solution is then added dropwise within 15 minutes, a pH of 11.4 being attained. The vitamin A acetate and triphenylphosphine oxide separate out. After stirring for 3 hours at room temperature (pH=10.7), the solution is neutralized to pH with about 8 ml. of a 2 N sulfuric acid (pH=8).

The further processing of the mixture is carried out as described in Example 1, there being obtained a yield of 98.1% of vitamin A acetate.

EXAMPLE 3

30 g. of β-ionylidenethyltriphenylphosphonium chloride are dissolved at 45° in 60 ml. of water, 9 g. of γ-acetoxytiglic aldehyde are subsequently added and, while stirring, the mixture is treated dropwise over a period of 15 minutes with 10 g. of potassium carbonate in 20 ml. of water. After stirring for 1 hour, the mixture is treated with methanol and extracted with n-hexane. After evaporation of the n-hexane, there remain 19.6 g. of vitamin A acetate consisting essentially of the all-trans isomer and the 11-cis isomer. The chemical yield amounts to 99.8%.

We claim:

1. A process for the preparation of vitamin A acetate which comprises reacting an aqueous solution of a salt formed by the reaction of vinyl-β-ionol and triphenylphosphine with an acid selected from the group consisting of sulfuric acid, a bisulfate, phosphoric acid and hydrochloric acid, with γ-acetoxytiglic aldehyde in the presence of a base.

2. A process according to claim 1 wherein said base is an alkali metal carbonate.

3. The process of claim 1 wherein said acid is selected from the group consisting of sulfuric acid, hydrogen sulfate and phosphoric acid, said reaction being carried out at about room temperature.

4. The process of claim 1 wherein said acid is hydrochloric acid and the reaction is carried out at about 35°–45° C.

5. A process for preparing vitamin A acetate which comprises reacting an aqueous solution of a salt formed by the reaction of vinyl-β-ionol and triphenylphosphine with an acid selected from the group consisting of sulfuric acid, hydrogen sulfate, phosphoric acid and hydrochloric acid, with γ-acetoxytiglic aldehyde in the presence of a base, the concentration of said salt in the aqueous solution being about one part of salt to about two parts of water.

6. The process of claim 1 wherein said base has a pK value of from about 8 to about 13.

* * * * *